United States Patent
Talebinejad et al.

(10) Patent No.: US 9,504,846 B2
(45) Date of Patent: Nov. 29, 2016

(54) CIRCUIT AND METHOD FOR USE IN TRANSCRANIAL MAGNETIC STIMULATION

(71) Applicants: Mehran Talebinejad, Ottawa (CA); Adrian D. C. Chan, Ottawa (CA)

(72) Inventors: Mehran Talebinejad, Ottawa (CA); Adrian D. C. Chan, Ottawa (CA)

(*) Notice: Subject to any disclaimer, the term of this patent is extended or adjusted under 35 U.S.C. 154(b) by 15 days.

(21) Appl. No.: 14/442,543

(22) PCT Filed: Nov. 13, 2013

(86) PCT No.: PCT/CA2013/050866
§ 371 (c)(1),
(2) Date: May 13, 2015

(87) PCT Pub. No.: WO2014/075183
PCT Pub. Date: May 22, 2014

(65) Prior Publication Data
US 2016/0213944 A1  Jul. 28, 2016

Related U.S. Application Data

(60) Provisional application No. 61/725,634, filed on Nov. 13, 2012, provisional application No. 61/790,267, filed on Mar. 15, 2013, provisional application No. 61/790,376, filed on Mar. 15, 2013.

(51) Int. Cl.
*A61N 2/02* (2006.01)
*A61N 2/00* (2006.01)

(52) U.S. Cl.
CPC ............... *A61N 2/02* (2013.01); *A61N 2/006* (2013.01)

(58) Field of Classification Search
CPC ........ A61N 2/00; A61N 2/004; A61N 2/006; A61N 2/008; A61N 2/02
See application file for complete search history.

(56) References Cited

U.S. PATENT DOCUMENTS

| 4,940,453 A | 7/1990 | Cadwell |
| 5,267,938 A | 12/1993 | Konotchick |

(Continued)

FOREIGN PATENT DOCUMENTS

EP  2167191 B1  12/2010

OTHER PUBLICATIONS

Rainoldi, A. et al., "A Method for Positioning Electrodes During Surface EMG Recordings in Lower Limb Muscles", Journal of Neuroscience Methods, Mar. 15, 2004, vol. 134, Issue 1, pp. 37-43.

(Continued)

*Primary Examiner* — Charles A Marmor, II
*Assistant Examiner* — Thaddeus Cox
(74) *Attorney, Agent, or Firm* — Brion Raffoul

(57) ABSTRACT

Systems, methods, and devices relating to transcranial magnetic stimulation (TMS). A circuit having at least two inductors is used in a TMS device. A small inductor adjacent to the patient's head and a large inductor away from the patient is used. The inductors are coupled to the circuit using multiple semiconductor switching subsystems. The subsystems, when activated, couple the inductors to the circuit and the inductors act as a single inductance. When deactivated, the subsystems decouple the inductors from the circuit and each inductor individually recovers or dissipates/discharges energy stored within. Since each inductor dissipates energy separately from each other, a much shorter dissipation or recovery time is achieved in the inductor close to the patient's brain as compared to the larger inductor. While dissipating or discharging, the small inductor induces electric currents in the brain to thus achieve stimulation and elicit action potentials.

23 Claims, 9 Drawing Sheets

(56) References Cited

U.S. PATENT DOCUMENTS

| | | | |
|---|---|---|---|
| 5,766,124 A * | 6/1998 | Polson | A61N 2/02 600/13 |
| 6,179,770 B1 | 1/2001 | Mould | |
| 6,551,233 B2 | 4/2003 | Perreault et al. | |
| 7,087,008 B2 | 8/2006 | Fox et al. | |
| 7,520,848 B2 | 4/2009 | Schneider et al. | |
| 7,711,431 B2 | 5/2010 | Tanner et al. | |
| 7,744,523 B2 | 6/2010 | Epstein | |
| 8,157,718 B2 | 4/2012 | Yi et al. | |
| 2007/0255085 A1 * | 11/2007 | Kishawi | A61N 2/002 600/9 |
| 2009/0018384 A1 * | 1/2009 | Boyden | A61N 2/02 600/13 |
| 2009/0105522 A1 * | 4/2009 | Yi | A61N 2/02 600/13 |
| 2010/0113959 A1 | 5/2010 | Pascual-Leone et al. | |
| 2010/0152522 A1 * | 6/2010 | Roth | A61N 2/02 600/13 |
| 2012/0029264 A1 | 2/2012 | Roth et al. | |
| 2012/0101366 A1 | 4/2012 | Ruohonen et al. | |
| 2013/0085316 A1 | 4/2013 | Fox et al. | |

OTHER PUBLICATIONS

Kendell, Cynthia et al., "A Novel Approach to Surface Electromyography: An Exploratory Study of Electrode-Pair Selection Based on Signal Characteristics", Journal of Neuroengineering and Rehabilitation, Apr. 26, 2012.

Hogrel, Jean-Yves, "Clinical Applications of Surface Electromyography in Neuromuscular Disorders", Clinical Neurophysiology, Jul. 2005, vol. 35, Issue 2-3, pp. 59-71.

Beck, Travis W. et al., "Electrode Placement Over the Innervation Zone Affects the Low-, Not the High-Frequency Portion of the EMG Frequency Spectrum", Journal of Electromyography and Kinesiology, Aug. 2009, vol. 19, Issue 4, pp. 660-666.

Zwarts, Machiel J. et al., "Multichannel Surface EMG: Basic Aspects and Clinical Utility", Muscle and Nerve, 2003, vol. 28, Issue 1, pp. 1-17.

Odagaki, Masato et al., "Precise Coil Positioning System Using Multi-Articular Arm for Location of Stimulated Brain Area in Transcranial Magnetic Stimulation", Proceedings of the 4th International IEEE EMBS Conference on Neutral Engineering, 2009.

Pozzo, M. et al., "Sixty-four Channel Wearable Acquisition System for Long-Term Surface Electromyogram Recording With Electrode Arrays", Medical and Biological Engineering and Computing Journal, 2004, vol. 42, Issue 4, pp. 455-466.

Disselhorst-Klug, Catherine et al., "Surface Electromyography and Muscle Force: Limits in sEMG—Force Relationship and New Approaches for Applications", Clinical Biomechanics, Mar. 2009, vol. 24, Issue 3, pp. 225-235.

Finni, Taija et al., "Variability in Lateral Positioning of Surface EMG Electrodes", Journal of Applied Biomechanics, Nov. 2009, vol. 25, Issue 4, pp. 396-400.

PCT International Search Report and Written Opinion of PCT/CA2013/050866, Feb. 3, 2014.

Peterchev, Angel V. et al., "A Transcranial Magnetic Stimulator Inducing Near-Rectangular Pulses With Controllable Pulse Width (cTMS)", IEEE Transactions on Biomedical Engineering, Jan. 2008, vol. 55, No. 1.

Lebossé, Cyrille et al., "A Robotic System for Automated Image-Guided Transcranial Magnetic Stimulation", Proceedings of the 4th International IEEE EMBS Conference on Neural Engineering, 2009.

Goetz, S. M. et al., "Analysis of a Novel Magnetic Stimulation System: Magnetic Harmonic Multi-Cycle Stimulation (MHMS)", International Conference on Biomedical and Pharmaceutical Engineering, 2009, pp. 1-6.

* cited by examiner

CIRCUIT AND METHOD FOR USE IN TRANSCRANIAL MAGNETIC STIMULATION

TECHNICAL FIELD

The present invention relates to transcranial magnetic stimulation (TMS). More specifically, the present invention relates to systems and circuits for use with TMS systems.

BACKGROUND OF THE INVENTION

The effectiveness of treatments for various mental and psychological ailments varies depending on the technology used and each technology has its drawbacks. Chemical treatments can only go so far while psychotherapy's effects take years before fruition. Magnetic or electric stimulation of the brain has shown very good results in mitigating if not reversing the effects of such ailments. However, implanted magnetic stimulators require invasive surgery while cranial electrotherapy stimulation has some undesirable side effects such as unpredictable memory loss.

Transcranial magnetic stimulation (TMS) has shown very promising results in the treatment of these ailments without the drawbacks or side effects of the other technologies. However, current TMS technology has some drawbacks as well. Current TMS technology requires that a capacitor or energy device to discharge its energy into an inductor. The inductor receives this energy and, as it does so, the inductor induces a magnetic field that produces electrical currents or action potentials in a patient's brain. Once the discharge from the capacitor is over, the inductor needs to recover from this discharge. The existing mono-phase pulses uses a rise time (when action potentials are elicited from the brain by way of the induced magnetic field) and decay during which the inductor recovers from the discharge. These charge and discharge cycles needed for the inductors used in current TMS technology have an confounding physiological effect due to the inductor recovery from the discharge. Currently, the amount of time required for the inductors to recover in TMS equipment is equal to or longer than the time required to discharge and elicit action potentials in the brain. Unfortunately, during this recovery time, further electrical currents in the brain are induced and these have been shown to have the above confounding physiological effects on the patient.

From the above, there is therefore a need for systems, methods, and devices which mitigates if not avoids the drawbacks of the prior art.

SUMMARY OF INVENTION

The present invention provides systems, methods, and devices relating to transcranial magnetic stimulation (TMS). A circuit having at least two inductors is used in a TMS device. A small inductor adjacent to the patient's head and a large inductor away from the patient is used. The inductors are coupled to the circuit using multiple semiconductor switching subsystems. In one embodiment, these subsystems include insulated gate bipolar transistors or IGBTs. The subsystems, when activated, couple the inductors to the circuit and the inductors act as a single inductance. When deactivated, the subsystems decouple the inductors from the circuit and each inductor individually recovers or dissipates energy stored within. Since each inductor dissipates energy separately from each other, a much shorter dissipation or recovery time in the inductor close to the patient's brain as compared to the larger inductor is achieved. While recovering or dissipating energy, the small inductor induces electric currents in the brain to thus achieve stimulation and elicit action potentials. In one embodiment, the smaller inductor acts as a stimulation or treatment coil and is used to deliver the magnetic stimulation to the patient's brain.

In a first aspect, the present invention provides a circuit comprising:
- at least two inductors, at least one of said inductors being for generating a magnetic field close to the patient's brain;
- an energy source for providing power to said at least two inductors;
- a plurality of semiconductor switching subsystems for directing power from said energy source to said at least two inductors to generate said magnetic field, said plurality of semiconductor switching subsystems directing energy to said at least two inductors when said subsystems are active;

wherein
- power is routed from said energy source to said at least two inductors only when all of said subsystems are active;
- when said subsystems are active, said at least two inductors operate as a single inductance;
- when said subsystems are inactive, each of said at least two inductors dissipates its stored energy as a single inductor;
- said subsystem comprises a power semiconductor switching device;
- said circuit is part of a magnetic stimulation device.

In a second aspect, the present invention provides a magnetic stimulation device comprising:
- a first inductor for use in providing a magnetic field adjacent a patient's skull;
- a second inductor for coupling to said first inductor, said second inductor being remote from said patient's skull;
- circuitry for providing electromagnetic pulse excitation to said inductors;
- an energy source for providing power to said first and second inductors;
- a plurality of semiconductor switching subsystems for directing power from said energy source to said first and second inductors to generate said magnetic field, said plurality of semiconductor switching subsystems directing energy to said first and second inductors when said subsystems are active;

wherein
- power is routed from said energy source to said first and second inductors only when all of said subsystems are active;
- when said subsystems are active, said at least two inductors operate as a single inductance;
- when said subsystems are inactive, each of said at least two inductors dissipates its stored energy as a single inductor.

In a third aspect, the present invention provides a method for providing magnetic stimulation to an area of mammalian tissue, the method comprising:
a) providing a transcranial magnetic stimulation device having a circuit comprising:
- at least two inductors, a treatment inductor for generating a magnetic field being one of said at least two inductors;
- an energy source for providing power to said at least two inductors;

a plurality of semiconductor switching subsystems for directing power from said energy source to said at least two inductors, said plurality of semiconductor switching subsystems directing energy to said at least two inductors when said subsystems are active;

b) energizing said energy source to provide power to said at least two inductors;

c) activating said plurality of semiconductor switching subsystems to thereby provide at least one energy pulse to said at least two inductors;

d) deactivating said plurality of semiconductor switching subsystems to thereby individually dissipate energy stored in said at least two inductors;

wherein power is routed from said energy source to said at least two inductors only when all of said subsystems are active;

when said subsystems are active, said at least two inductors operate as a single inductance;

when said subsystems are inactive, each of said at least two inductors dissipates its stored energy as a single inductor;

said subsystem comprises a power semiconductor switching device;

a magnetic field is induced in said mammalian tissue when said stored energy in said treatment inductor is being dissipated.

In a fourth aspect, the present invention provides a method for producing a magnetic field in mammalian tissue, the method comprising:

a) providing a magnetic stimulation device having a circuit comprising:

at least two inductors, a treatment inductor for generating a magnetic field being one of said at least two inductors;

a plurality of semiconductor switching subsystems for charging and discharging said at least two inductors;

b) activating said plurality of semiconductor switching subsystems to charge said at least two inductors;

c) deactivating said plurality of semiconductor switching subsystems to individually discharge said at least two inductors;

wherein when said subsystems are active, said at least two inductors operate as a single inductance;

when said subsystems are inactive, each of said at least two inductors dissipates its stored energy as a single inductor;

a magnetic field is induced in said mammalian tissue when said stored energy in said treatment inductor is being dissipated.

In a fifth aspect, the present invention provides a method of mapping a subject's head for use in locating at least one area on said head for treatment, the method comprising:

a) determining a plurality of registration points on said subject's head;

b) receiving coordinates of each of said plurality of registration points, said coordinates being gathered by sequentially placing one end of a robotic arm at each of said registration points and determining location coordinates of said one end of said robotic arm;

c) creating a reference model of said subject's head using said coordinates;

d) registering said reference model with a previously created treatment model of said subject's head such that corresponding points align between said reference model and said treatment model;

wherein said treatment model is created to determine which areas require treatment.

In a sixth aspect, the present invention provides a pad for use in sensing and sampling bioelectric signals, the pad comprising:

a 2 dimensional array of sensor pads, each sensor pad being attached to at least one other sensor pad, each sensor pad comprising:

a backing having two sides;

a bioelectric sensor attached to a first side of said backing;

a connection coupler attached to a second side of said backing, said connection coupler being electronically coupled to said bioelectric sensor, said connection coupler being for coupling said bioelectric sensor with bioelectric sensing equipment;

wherein said pad has at least 2 sensor pads across widthwise and has at least 2 sensor pads across lengthwise;

said pad is disposable.

In a seventh aspect, the present invention provides a system for gathering bioelectric data from a human being, the system comprising:

a 2 dimensional array of sensor pads, each sensor pad being attached to at least one other sensor pad, each sensor pad comprising:

a backing having two sides;

a bioelectric sensor attached to a first side of said backing;

a connection coupler attached to a second side of said backing, said connection coupler being electronically coupled to said bioelectric sensor;

a bioelectric data gathering module comprising:

a plurality of connector couplers for coupling with connection couplers on said array of sensor pads;

a signal amplifier for amplifying said signals an analog/digital converter for converting analog signals into digital signals;

an external interface submodule for communicating with equipment external to said system;

wherein said array of sensor pads has at least 2 sensor pads across widthwise and has at least 2 sensor pads across lengthwise.

BRIEF DESCRIPTION OF THE DRAWINGS

The embodiments of the present invention will now be described by reference to the following figures, in which identical reference numerals in different figures indicate identical elements and in which.

DETAILED DESCRIPTION OF THE INVENTION

It should be noted that the term "model" in this document is meant to refer to a computer model viewable on a suitable monitor or viewing device. Preferably, the models referred to in this document are three-dimensional (3D) models.

It should also be noted that the term "bioelectric signals" refers to electrical activity generated by biological tissue such as muscle cells, neurons, and endocrine cells and which can be measured and detected by way of sensors on a subject's skin. Surface electromyography (sEMG), electrocardiography (ECG or EKG), and electroencephalography (EEG) are just three subject areas which are based on the detection and measurement of electrical activity in a biological subject.

Figure 1:
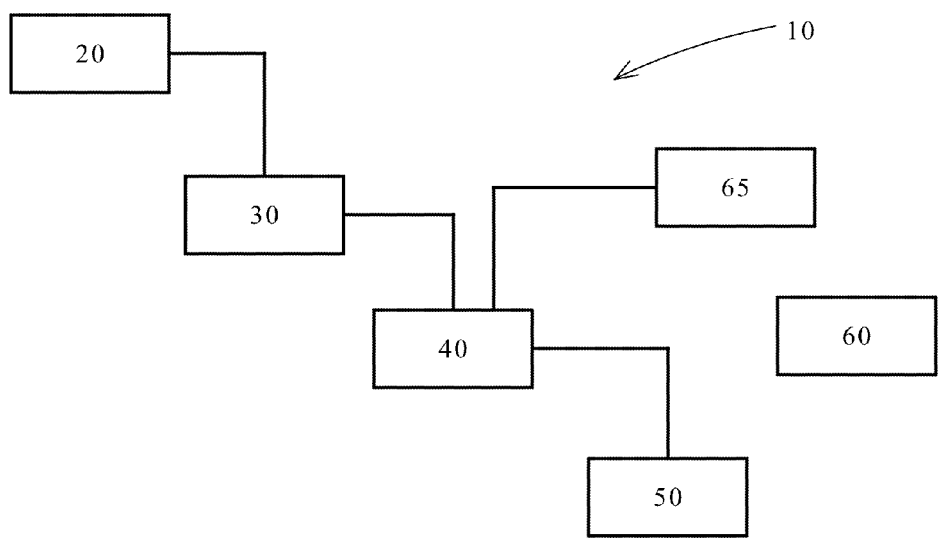
FIG. 1 is a block diagram of a transcranial magnetic stimulator system.

Referring to FIG. 1, a block diagram of a transcranial magnetic stimulator is illustrated. As can be seen, the system 10 has a power source 20, and energy source 30, circuitry 40, and an inductor 50. The power source 20 energizes the energy source 30. Using circuitry 40, the energized energy source 30 provides electromagnetic power to the coil 50 that produces a magnetic field. The magnetic field is applied to a patient's skull 60. A second inductor 65 may form part of the circuitry 40.

As is well known, the electromagnetic power may be applied as pulses such that the magnetic field applied to the patient's skull is also pulsed. The duration and strength of the magnetic field may be controlled depending on the treatment requirements.

Figure 2:
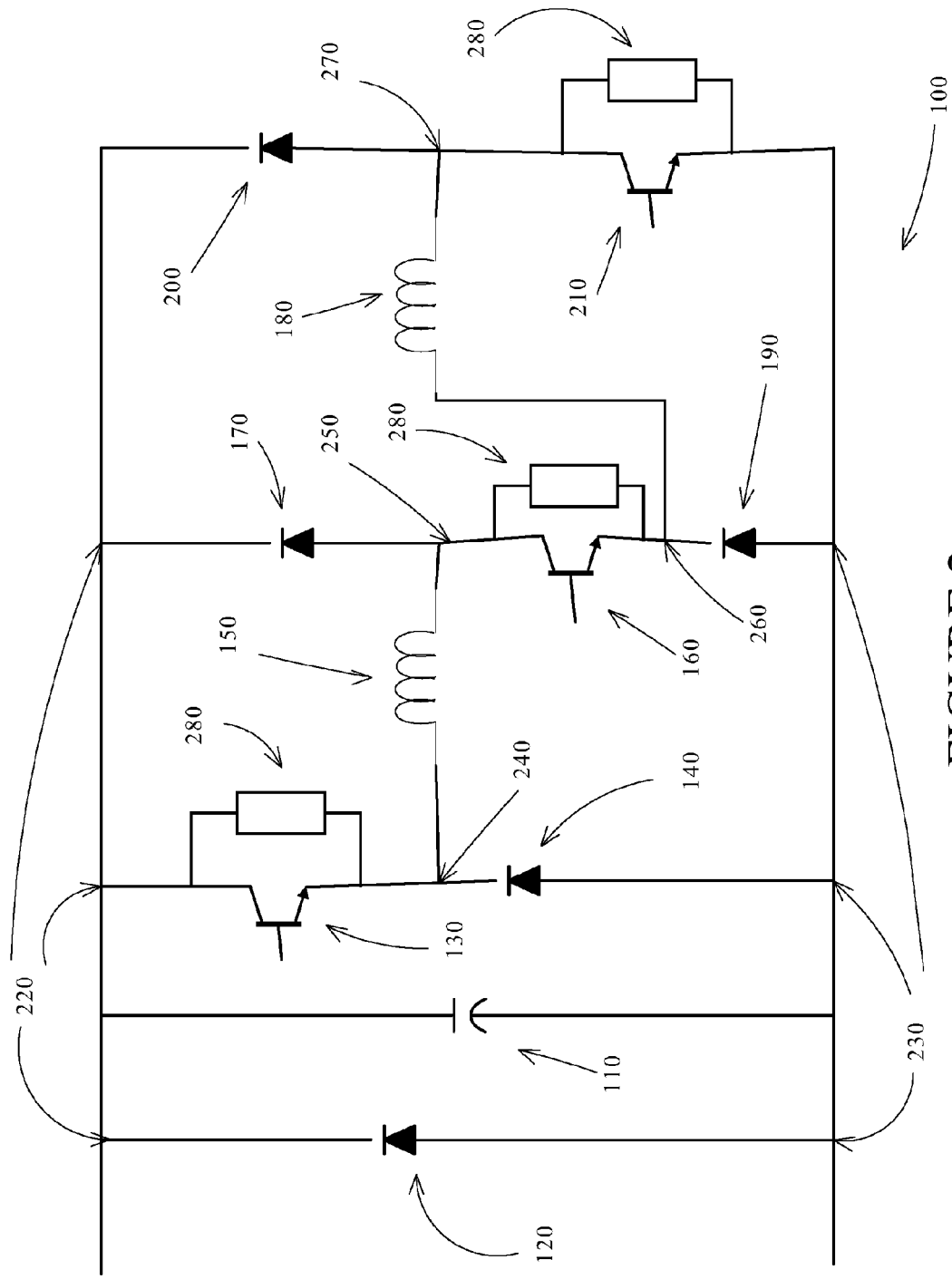
FIG. 2 is a circuit diagram of a circuit according to one aspect of the invention and which may be used in the TMS system in FIG. 1.

Part of the circuit 40 is the circuit illustrated in FIG. 2. The circuit 100 has a capacitor 110, a first diode 120, a first semiconductor switching subsystem 130, a second diode 140, and a first inductor 150. The circuit 100 also has a second semiconductor switching subsystem 160, a third diode 170, a second inductor 180 and a fourth diode 190. Finally, the circuit 100 has a fifth diode 200 and a third semiconductor switching subsystem 210.

In the circuit 100, the diode 120 is coupled between the input nodes 220, 230. Capacitor 110 is also coupled between nodes 220, 230. The collector of the first semiconductor switching subsystem 130 is coupled to node 220 while the emitter of this first semiconductor switching subsystem 130 is coupled to node 240. Diode 140 is coupled between node 240 and node 210. First inductor 150 is coupled between node 240 and node 250. The collector of the second semiconductor switching subsystem is coupled to node 250 while diode 170 is coupled between node 250 and node 220. The emitter of the second semiconductor switching subsystem 160 is coupled to node 260 and diode 190 is coupled between node 260 and node 230. Second inductor 180 is coupled between node 260 and node 270. Diode 200 is coupled between node 220 and node 270. The collector of the third semiconductor switching subsystem 210 is coupled to node 270 while the emitter of the third semiconductor switching subsystem 210 is coupled to the node 230.

In one implementation of the circuit 100, all the semiconductor switching subsystems are commonly gated or are controlled by a common gating signal. This means that all the semiconductor switching subsystems are simultaneously active or inactive. All the semiconductor switching subsystems can thus be activated or deactivated with a single signal.

It should be noted that each semiconductor switching subsystem may be equipped with an anti-parallel diode 280 coupled between each semiconductor switching subsystem's collector and emitter.

As is well-known in the electronic arts, semiconductor switching devices are "active" when they are conducting and "non-active" or "inactive" when they are not conducting. In more detail, semiconductor devices, especially transistors, conduct across their collector and emitter nodes depending on the voltage applied to their gate node (i.e., control signal). When a semiconductor switching device is conducting, the device is considered "active". When a semiconductor switching device is not conducting across its collector and emitter nodes, the device is considered "non-active" or "inactive" or "deactivated".

Also in the circuit, the capacitor 110 operates as an energy storage device which discharges its energy to the inductors 150, 180. To generate the electromagnetic pulses required for TMS or most forms of magnetic stimulation, the capacitor has to charge and discharge repeatedly. The duration of the discharges is usually in the order of micro-seconds. The pulses may be repeated at frequencies between 1 to 1000 Hz.

In circuit 100, input nodes 220, 230 are coupled to a power source from which the capacitor 110 is charged. To discharge the energy of capacitor 110 into inductors 150, 180, all the semiconductor switching subsystems are active, thereby allowing current to pass through the inductors 150, 180. Once the pulse is done, all the semiconductor switching subsystems are deactivated or rendered inactive simultaneously. This causes the current within each inductor 150, 180 to be zero (i.e. very small). Normally, a single inductor with an inductance equal to the combined inductances of the first and second inductors would require a certain amount of time in which to dissipate its current after the single inductor has been disconnected from a circuit. By splitting the inductance into two separate inductors and simultaneously disconnecting both inductors, each inductor can dissipate its current independently and separately from the other. Accordingly, the effective amount of time required to dissipate the current from the two separate inductors is less than the amount of time required to dissipate the current from a single inductor with the same inductance as the two inductors. This is because, instead of having to dissipate current from a single inductor, each separate inductor dissipates its current in parallel (yet separately) with the other inductor.

It should be noted that when all the semiconductor switching subsystems are active, the two inductors 150, 180 operate as a single, combined inductance. However, when the semiconductor switching subsystems become inactive, each of the two inductors 150, 180 operates as an independent inductor.

It is preferred that the semiconductor switching subsystems are implemented as insulated gate bipolar transistors (IGBTs). While not ideal, MOSFETs may also be used as semiconductor switching devices. Diodes are used throughout the circuit 100 as recovery circuit elements. Again, while not ideal, thyristors may also be used in place of the diodes in FIG. 2.

In one implementation, one of the inductors (the first inductor) operates as the coil 50 while the other inductor may be located physically remote from the coil 50. One of the inductors may thus be adjacent to a patient's skull during treatment while the other inductor is located with the rest of the TMS circuitry and apparatus.

Regarding the inductance of the first and second inductors, it is preferred that their inductances are not equal. In fact, it is preferred that their inductances be at a ratio of between 1:10 to 1:20 to each other. For clarity, the inductance of the first inductor is preferred to be 1/10th to 1/20th of the inductance of the second inductor.

In operation, the circuit is coupled to a power source. The capacitor is charged and, once charged, is discharged into the two inductors. This discharge is done when the semiconductor switching subsystems are active. The current in the inductors is used to create a magnetic field that is applied to the patient's skull. After the magnetic field has been applied, all the semiconductor switching subsystems are deactivated, thereby electronically isolating the two inductors from the circuit. Each inductor then independently dissipates its stored energy. The process can then repeat for each electromagnetic pulse needed for patient treatment.

It should be noted that while FIG. 2 and the description above discusses two inductors in the circuit, other variants are, of course, possible. Systems which use three or more inductors, with an attendant increase in the number of semiconductor switching subsystems, are possible. In these variants, multiple inductors may be located adjacent to the patient's skull. Similarly, multiple inductors may be located as part of the circuit and may thus be located remotely from the patient's skull.

In operation, the discharge of the capacitor causes a current to pass through the inductors. The time during which this is occurring can be termed the rise time as energy is stored in each inductor's magnetic field. During this time, the semiconductor switching subsystems are active or activated. When the capacitor's discharge is done, the semiconductor switching subsystems are deactivated and the inductors are isolated from the rest of the circuit. This causes the energy in the inductors to be dissipated with each inductor dissipating its energy independently and separately from the other inductor or inductors. This period of energy dissipation can be termed the decay or recovery period as the energy stored in each inductor's magnetic field decays as the inductor recovers from the capacitor's discharge.

For one implementation, as noted above, the first inductor (acting as the treatment coil) has an inductance that is 1/10 to 1/20 of the inductance in the circuitry. For this configuration, the rise time is extended and is, comparatively speaking, long. The decay time for the small or first inductor is quite small compared to the decay time for the large or second inductor. The action potential or effective electrical field induced in the patient's brain is achieved during the decay time for the small inductor.

Figure 3:
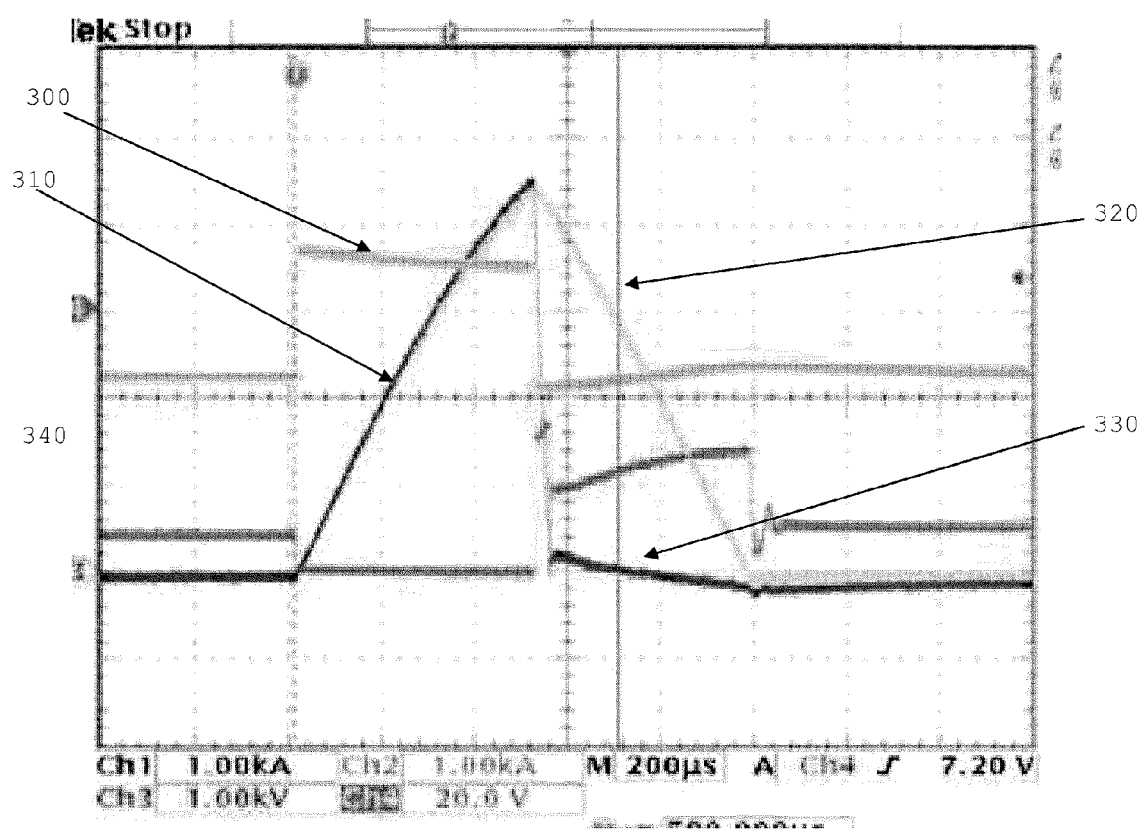
FIG. 3 is a diagram of a number of waveforms illustrating the signals produced for a charge/discharge cycle for the circuit in FIG. 2.
Figure 4:
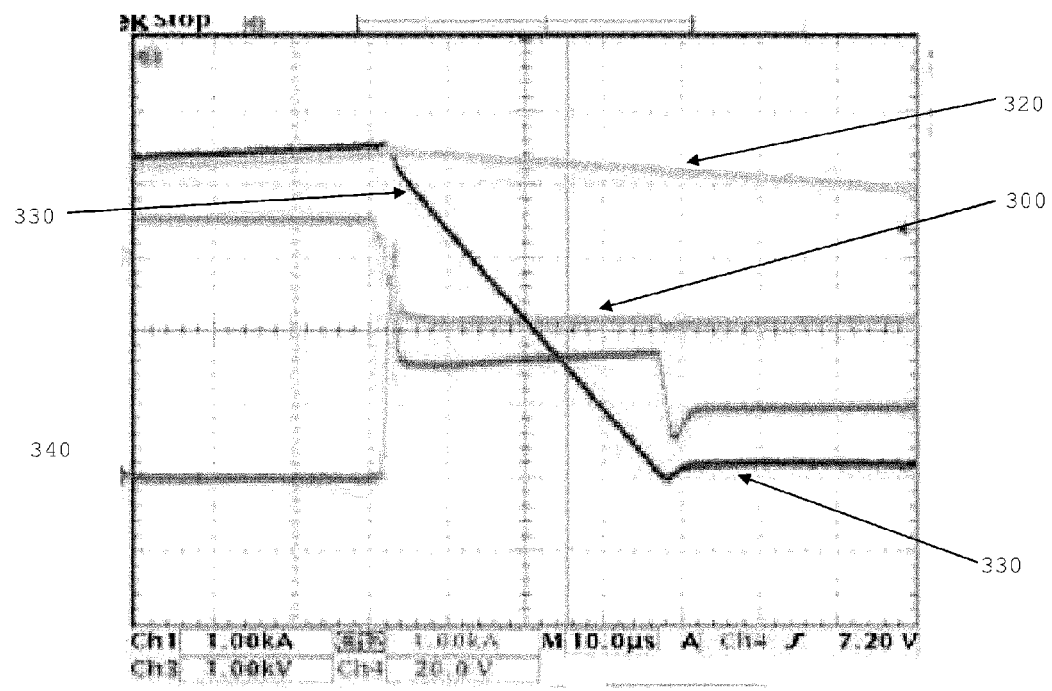
FIG. 4 is a detailed view of one section of FIG. 3 showing the effects of the short discharge time for the treatment inductor shown in FIG. 2.

Referring to FIGS. 3 and 4, waveforms for the circuit in operation are presented. Referring to FIG. 3, the waveform 300 for the gates in the circuit are illustrated. Along with waveform 300, the waveform 310 for the rise time of the inductors is shown as well as the waveform 320 for the decay time for the inductor 150 and the waveform 330 for the decay time of the inductor 180.

As can be seen from FIG. 3, the rise time of the inductors 150, 180 is similar in duration and starts once the switching subsystems are activated (see waveform 310). Once the switching subsystems have been deactivated, the decay time for inductor 150 is much smaller than the decay time for inductor 180. This can be seen by comparing waveform 320 with waveform 330. Waveform 330 shows that the decay time for inductor 150 is but a fraction of the decay time for inductor 180.

Referring to FIG. 4, a much closer view of the waveforms is presented. As can be seen, waveform 330 shows that the current in inductor 150 decays sharply once the switching subsystem is deactivated (see waveform 300). Conversely, the current in inductor 180 slowly decays after the switching subsystem is deactivated (see waveform 320). Since there is no confounding physiological effects after the current decay from the smaller inductor 150, it is advantageous to derive the action potential or effective electrical field during the current decay from the smaller inductor as the inductor discharges. This is in contrast to current technology where the action potential is derived from the rising time as an inductor charges. In current technology, the benefits from the action potential derived from the rising time as an inductor charges is counteracted by the physiological effects due to the long discharge time of the inductor. By deriving the action potential from the comparatively short decay time as the smaller inductor discharges, the action potential is not counteracted by physiological effects from a long decay time.

It should be noted that current mono-phase technology used in TMS applications have short rise times and long decay times as the inductors used are rapidly charged and then slowly discharged. The magnetic field induced by the charge and discharge of inductors in current technology are similar in shape to the charge/discharge waveform for the current in the inductor—these are characterized by short charging times and long discharging times. The present invention provides long charge times but very short discharge times as the discharge times are determined by the size of the inductors used. Since the magnetic field produced by the smaller inductor is proportional to the current in this smaller inductor and since the electrical field induced by this magnetic field is proportional to the magnetic field rate of change, the electrical field has a narrow rectangular shape and is proportional to the voltage across the device. This narrow rectangular shape can be seen as part of waveform 340 and can be seen in more detail in FIG. 4. The electrical field produced by the magnetic field in the mammalian tissue being treated is therefore characterized as a short, sharp pulse which mostly lasts only as long as the smaller inductor 150 (or the treatment inductor) is discharging or as long as the current in the smaller inductor is decaying.

To assist in the above described system, a novel system for positioning magnetic coils for TMS treatment is also provided as part of the invention. Current TMS methods are based on manual positioning of these electromagnetic coils on the subject's head.

To determine where to place the magnetic coils, a model of the subject's head is created. This is done by placing multiple fixed video cameras near the subject's head and placing markers on the head. The various views of the subject's head are then used to create the model. Once the model has been created, physicians can then determine where on the subject's head should the electromagnetic coils be positioned. Unfortunately, this process may be fraught with inaccuracies as the subject may move his or her head when the cameras are seeking to locate the markers on the head.

Once the placement of the coils have been determined, physically positioning these coils during treatment can also be tricky. Currently, a physician or other medical personnel will need to hold the coil in place while the treatment is being administered. Given that the coils can be quite heavy and that treatment can last from seconds to minutes, this can be tiring and thereby prone to errors. One alternative would be to have a stationary holder for the coil as the treatment progresses. Unfortunately, this is also fraught with issues as the placement of the coil itself can be problematic. The placement can only be as good as the person locating the coil on the subject's head. This person must, with the help of the model and the physician's indication of where to place the coil, locate that point on the subject's head and hold that coil at that precise location while treatment is being administered.

In the novel coil placement system and method for positioning electromagnetic coils relative to a subject's head for transcranial magnetic stimulation, a robotic arm is used with specific registration points on the subject's head to construct a model of the head. A user can position one end of the robotic arm at each one of the multiple predetermined registration points on the user's head and the coordinates for this position is recorded. Once all the coordinates for the registration points are recorded, the system can generate a suitable reference model for the head. The reference model for the subject's head can then be used in conjunction with a previously constructed treatment model which was used for determining the subject's diagnosis and treatment regimen. The reference model and the treatment model can then be co-registered with each other so that corresponding points on each model correspond with one another. Thus, a point on the reference model's forehead will register with the same point on the treatment model.

The reference model can be used in multiple ways. Once the reference model has been co-registered with the treatment model, tracking the position of the robot arm on the subject's head by way of the reference model allows for easier placement of the coil on the subject's head. By overlaying the reference model with the treatment model, a user can easily visualize the location of the treatment area. Since the coordinate system on the reference model is known to the system, tracking the robot arm's position on the reference model is simple and can be easily displayed on the reference model. By highlighting the designated treatment area on the treatment model and overlaying the two models, a user can determine how far or how close the robot arm is to the designated treatment area. Positioning the robot arm precisely at the designated treatment area can therefore be done and, by attaching the coil to the end of the robot arm, precise placement of the coil is thus now possible.

The reference model can also be used in conjunction with the robot arm for the actual treatment process. Given the co-registration between the reference model and the treatment model, the treatment area denoted on the treatment model can be programmed into the reference model after the co-registration. The robot arm can then be programmed to position its end to the coordinates of the treatment area. The robot arm can also be programmed to remain at those coordinates for a predetermined amount of time. By attaching a coil to the robot arm, the robot can be used to deliver the required treatment regimen to the subject.

In addition to the above, the reference model and the robot arm can be used to deliver multiple treatment regimens for multiple subjects. Each subject can have his or her own reference and treatment models stored in digital storage including the treatment model's treatment area. A suitable program can then be used with a coil equipped robot arm to have the robot arm deliver the required treatment regimen to the subject.

Figure 5:
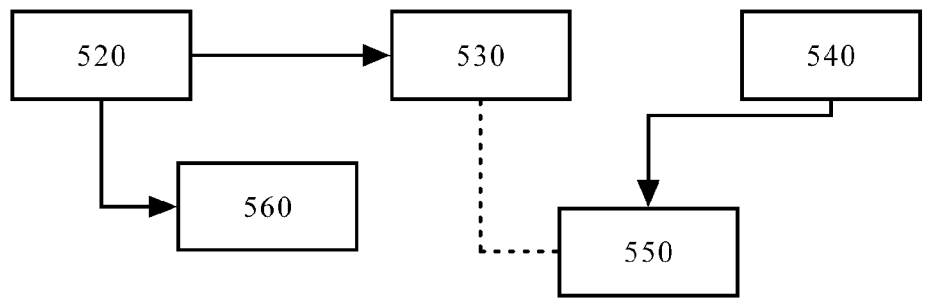
FIG. 5 is a block diagram of a system according to one aspect of the invention.

Referring to FIG. 5, a block diagram of a system which uses the present invention is illustrated. As can be seen, the system 510 includes a control system 520, a robot arm 530, a TMS treatment subsystem 540, and a treatment coil 550. A model construction subsystem 560 is also present. The control system 520 controls the robot arm 530 and can determine the coordinates in space for the end of the robot arm. The control system 520 can also place and hold the end of the robot arm at any suitable coordinate in space reachable by the robot arm. The TMS treatment subsystem includes the treatment coil 550 through which magnetic fields can be projected. The model construction system interfaces with the control system to accept the coordinates entered into the control system. The model construction system can create a reference model of a subject's head based on coordinates from the control system.

In operation, the user first has to register the coordinates of specific registration points on the subject's head. As an example, the user brings the robot arm (either manually or by use of controls on the control system) to the subject's forehead (at a point between the eyebrows), to the crown of the subject's head, to the back of the subject's neck (the base of the skull), and to each of the subject's ears. Alternatively, the robot arm can be brought to the left and right ears and the bridge of the nose as the specific registration points. At each one of these registration points, the user registers the coordinates with the control system. This can be done by the user manually registering the coordinates (i.e. activating a button or switch on the control system). Once the coordinates for all the registration points have been entered, the model construction subsystem 60 can use these coordinates to constructed a reference model of the subject's head. The construction of a model of a subject's head given a number of reference points on the subject's head is well-known in the art and can be performed using off-the-shelf software.

It should be noted that the number and location of these registration points are dependent on the configuration of both the model construction subsystem and the software used for constructing the reference model. Other means for gathering the data from the subject's head for the construction of the reference model are, of course, possible. As an example, instead of discrete registration points, the subsystem may use a continuous listing of coordinates as the user traces the outline of the subject's head using the robot arm.

Once the model construction subsystem 560 has constructed the reference model of the subject's head, the reference model is then co-registered with the treatment model. The treatment model is a pre-existing model of a human head which is used by a physician in diagnosing the subject and in determining the treatment locations on the subject's head. For ease of reference, most physicians indicate the treatment locations or areas on the treatment model.

To co-register the reference model with the treatment model, multiple well-known methods can be used. As an example, specific points which are on specific features common to both models can be determined and correlated on both models. Thus, as an example, the point midway between the eyebrows, the crown of the head, the location of the ears, and the base of the back of the skull can be used as reference points. By lining up these reference points on both models, the two models can be co-registered with each other such that corresponding points on the two models align with each other. Of course, other methods for co-registering the two models are possible and can be used with the invention.

With the two models co-registered, a user can take advantage of the co-registration to track the robot arm's position relative to the subject's head. The two models can be overlaid to one another so that the treatment area can be seen on the reference model. The location of the robot arm can then also be illustrated on the reference model. As the user moves the robot arm (whether manually or by using the controls on the control system or by using a preprogrammed movement pattern), the user can see how far or how close the robot arm's end is to the treatment area. By attaching the coil to the end of the robot arm, the coil's position relative to the desired treatment area can now be viewed on the overlaid models. A user can thus determine the amount and direction of movement required by the robot arm to place the coil in the treatment area.

The tracking of the robot arm's position and the programmability of the robot arm can also be taken advantage of by having the robot arm deliver the treatment regimen to the subject. Once the two models are co-registered, the coordinates for the treatment area can be extracted from the treatment model. The robot arm can therefore be programmed to position its coil-equipped end at the treatment area for the amount of time required by the treatment regimen. This programmed behavior by the robot arm is repeatable and can be used to deliver multiple instances of a specific treatment regimen to a specific subject. The specific subject's treatment model and reference model can be stored in digital storage along with the programmed steps required of the robot arm to deliver the treatment regimen. When the subject returns for subsequent treatment, the relevant models and programming can be retrieved and used to treat the subject.

It should be noted that some treatment regimens require multiple treatment areas on the same subject. For such regimens, it was previously thought that multiple TMS machines were required, with each TMS machine treating a specific treatment area. However, the use of the programmability characteristic of the robot arm and the reference and treatment models allows for a single TMS machine to deliver the same treatment regimen as multiple machines. A robot arm can be programmed to position the coil at one treatment area for a given period of time and then move to another treatment area for another period of time. This can be repeated as many times as necessary for as many treatment areas as possible for a single subject.

Regarding the equipment to be used in the working of the invention, the model construction subsystem can be a suitable general purpose computing device with suitable software for model construction. Of course, this subsystem needs to be interfaced with the control system for the robot arm so that the subsystem can receive the relevant coordinates for the reference points on the subject's head. The selection and use of the model construction subsystem is well within the skill set of a person skilled in the art.

It should be noted that the model construction subsystem and the reference and treatment model generator can be similar to the visor2™ product from ANT Neuro (www.antneuro.com) in the Netherlands and may use similar model construction subroutines and algorithms. A software package similar to this product may also be used for neuronavigation or for navigating either one of or both of the reference and treatment models.

Regarding the robot arm, in one implementation, the robot arm manufactured by KUKA Roboter GmbH as Lightweight Robot 4 (LWR 4) was found to be suitable. This product is a 7-axis jointed arm robot and can be operated with position, velocity, and torque control. Each of the joints has a position sensor on the input side and position and torque sensors on the output side. The Lightweight Robot 4 has five joint modules, a base frame, and a 2-axis in-line wrist. Systems and devices similar to this product and with capabilities comparable to this product may be used to implement the invention.

Figure 6:
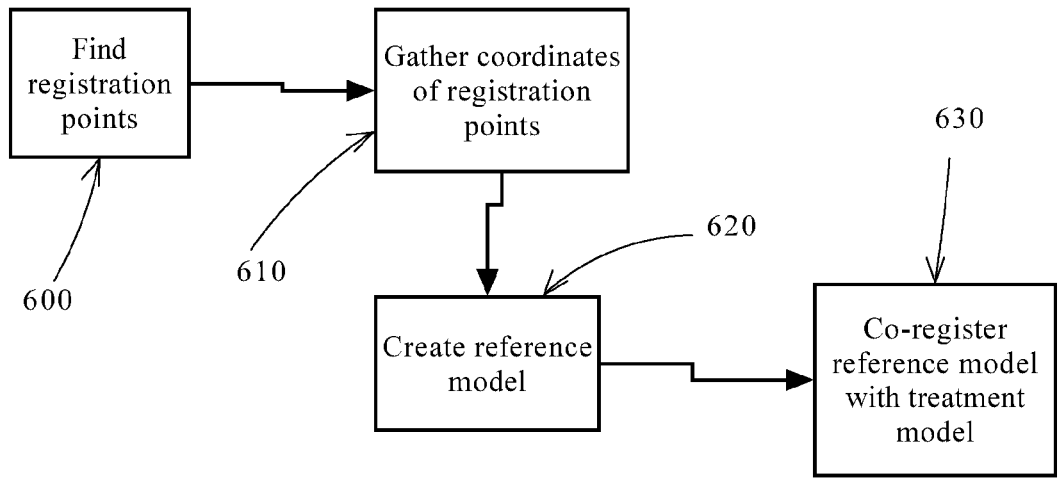
FIG. 6 is a flowchart detailing the steps in a method according to another aspect of the invention.

Referring to FIG. 6, a flowchart detailing the steps in a method according to one aspect of the invention is illustrated. The process starts with step 600, that of finding specific registration points on the subject's head. This step may use predetermined registration points (e.g. the subject's ears and bridge of the nose) or arbitrary registration points which, when taken together, define at least part of the subject's cranium.

With the registration points found, step 610 gathers the 3D (three dimensional) coordinates of these various registration points. This can be done by sequentially placing the end of the robot arm at each of the registration points and then triggering the control system to take note or store of the coordinates of the position for the end of the robot arm. By storing the coordinates of the various registration points, these coordinates can be the basis of the reference model to be created.

Step 620 is that of creating the reference model. The reference model is created based on the coordinates of the various registration points on the subject's head. Well known methods and algorithms for creating a hemispheric model of the subject's head can be used for this step.

After the reference model has been created, step 630 is that of co-registering the reference model with the treatment model containing the data as to the treatment areas for the particular subject. The process of co-registering the reference model with the treatment model involves matching corresponding points from one model with points on the other model. The models are then manipulated and aligned with one another until points on one model align and match with corresponding points on the other model.

When the two models are aligned and co-registered, the images of both models can be overlaid one another to present a single image to be used by the user. The points of interest on each of the models can now be seen in relation to other points of interest. As an example, the treatment area shown on the treatment model can now be viewed in relation to the position of the robot arm's end shown on the reference model.

To assist the user in determining a patient's readings and vital signs for, among other things, preparing for the use of the above systems, the present invention also provides a novel sensor pad configuration. Current technology only uses single sensor pads to detect and measure bioelectric signals. These single sensor pads can be difficult to place—technicians or physicians who have a detailed knowledge of anatomy are usually required to position the sensor pads for optimal bioelectric readings. Of course, such professionals are not infallible and it is not unusual for multiple attempts before a suitable signal can be detected and measured. This requirement that a physician attend to a task as mundane as the placement of sensors on a subject's body can be seen as a very inefficient use of available resources.

Also, while current technology allows for the use of multiple single sensor pads to cover an area from which bioelectric signals are to be detected and measured, each sensor pad typically requires at least one lead or line to the bioelectric detection equipment. Multiple sensor pads can therefore lead to a tangled mess of wires which can be confusing if not dangerous to the subject and those operating the equipment. The use of multiple sensor pads can also lead to variations in signal due to the variation in sensor pad spacings.

This aspect of the invention provides systems, methods, and devices relating to the detection and gathering of data for bioelectric signals. A disposable two-dimensional array of sensor pads is provided. Each of the sensor pads in the array has a backing with a sensor on a first side and a connection coupler on a second side. The first side is coated with a conductive gel and the sensor pad array is adhesively attachable to a subject's skin. The connection coupler is usable with various electrical coupler systems such as those which use a snap-on connector. The two-dimensional array has at least two sensor pads lengthwise and at least two sensor pads widthwise. The array may be used with a bioelectric data gathering module. The module may be self-contained and attachable to the sensor pad array. The module may include storage on to which the data relating to the detected and measured bioelectric signals can be stored. Similarly, the module may work with external equipment which can analyze and store the data.

Figure 7:
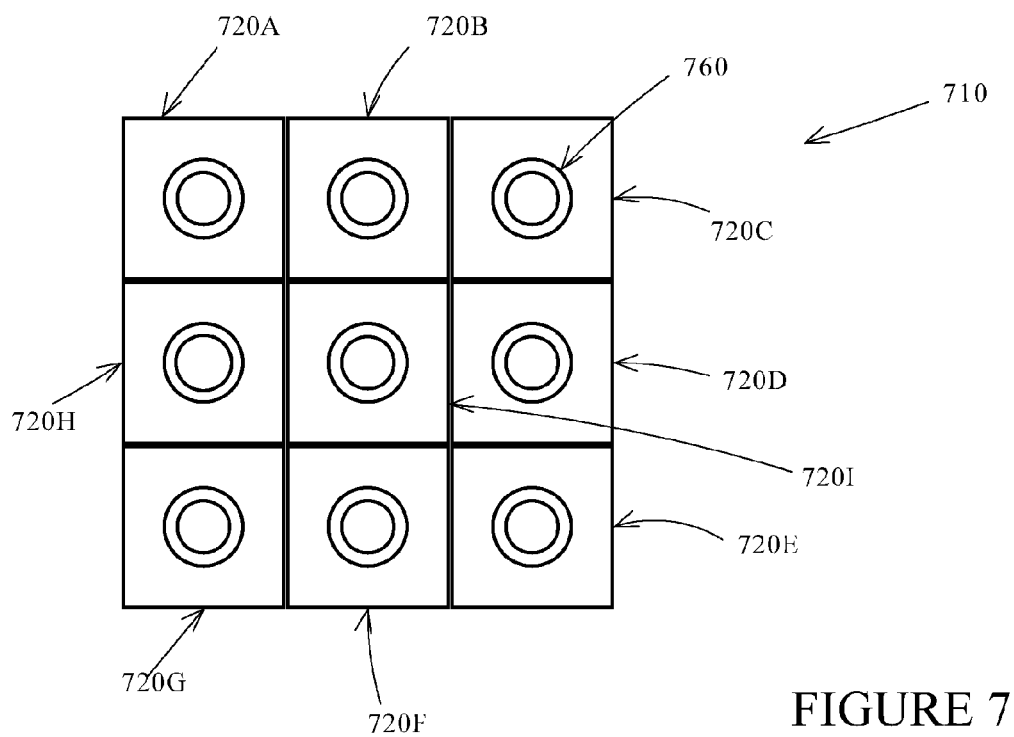
FIG. 7 is a top plan view of a pad for use in detecting and measuring bioelectric signals according to one aspect of the invention.
Figure 8:
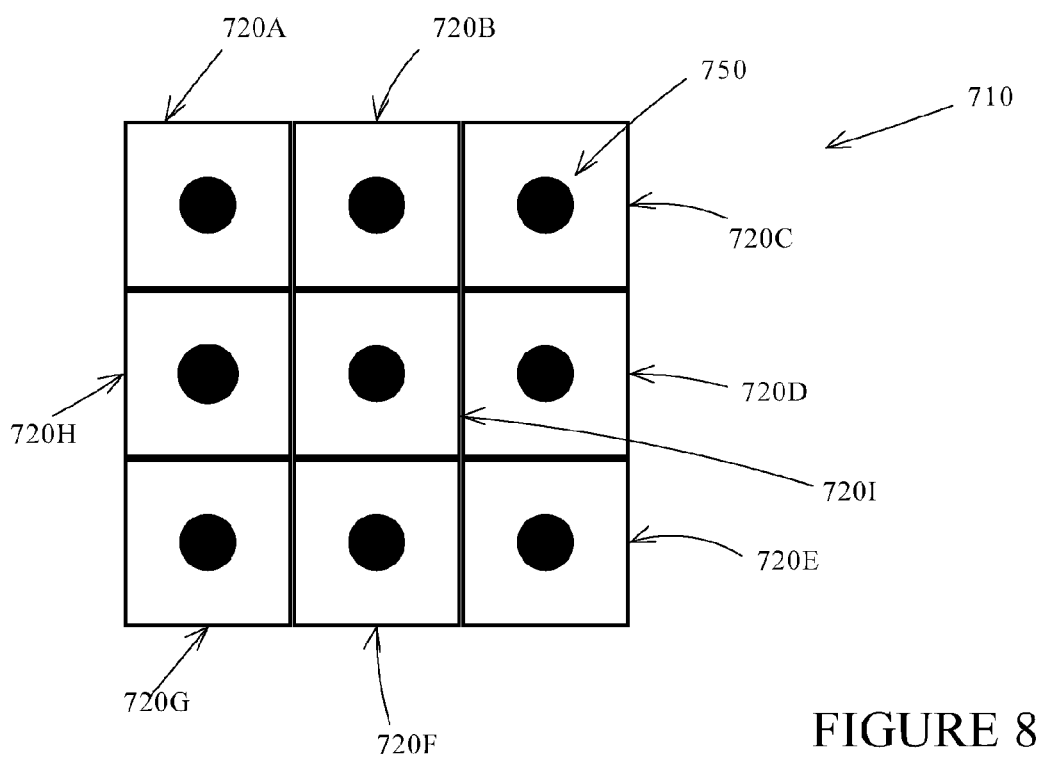
FIG. 8 is a bottom plan view of the pad illustrated in FIG. 1.
Figure 8A:
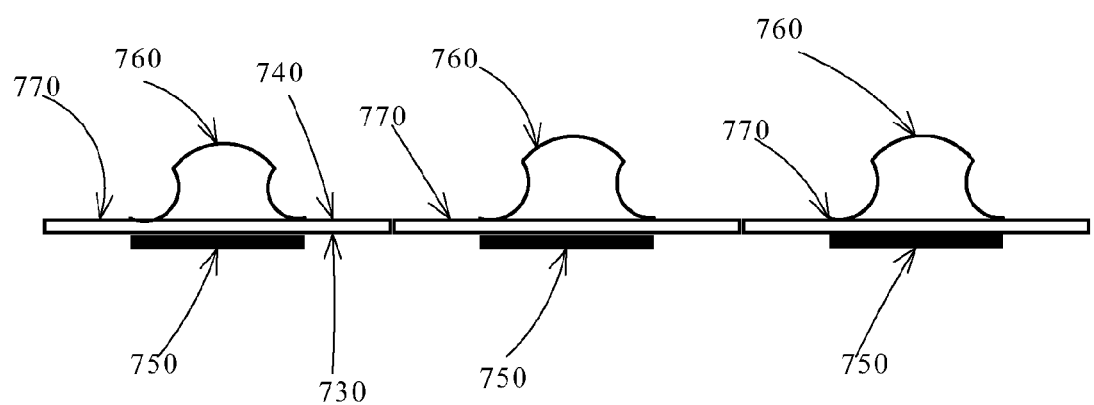
FIG. 8A is a side view of the pad in FIG. 1.

Referring to FIG. 7, a top plan view of a pad according to one aspect of the invention is illustrated. FIG. 8 is a bottom plan view of the pad in FIG. 7. FIG. 8A is a side view of the pad in FIG. 7. The pad 710 is a two-dimensional array of sensor pads. In FIG. 7, the pad 710 has three sensor pads in a lengthwise direction and three sensor pads in a widthwise direction. The pad 710 in FIG. 7 is a 3×3 configuration but the pad can be as small as a 2×2 configuration. A rectangular configuration as opposed to the square configuration in FIGS. 7 and 8 is also possible. It should be clear that the pad 710 in FIG. 7 is a low density two-dimensional array of sensor pads.

Each sensor pad 720A, 720B, 720C, 720I has a first side 730 and a second side 740. Each sensor pad 720A-720I has a sensor 750 on the first side and a connection coupler 760 on the second side. The sensor 750 and connection coupler 760 are set on a flexible backing 770. The sensor 750 may be a Ag—Ag/Cl (silver-silver chloride) sensor which is well-known to the person skilled in the art. Other suitable sensors may also be used. The connection coupler illustrated in the figures is a metallic conductor which is of a snap-on type connector well-known to the person skilled in the art. Other types of connectors may also be used as the connection coupler. As an alternative, instead of a single button snap connector, the array may have a smaller electrical interface. For such an option, instead of a single connector per electrode, a single connector that connects all the sensors to the external circuitry could be used.

The first side of each sensor pad may be coated with a conductive gel to assist in the sensor sensitivity to the bioelectric signals. As well, at least part of each sensor pad may also be coated with a suitable adhesive so that the sensor pad may adhere to a subject's skin.

When in use, the pad 710 may be placed in the region of where a bioelectric signal is to be measured or detected. In one example, the electrical activity of specific arm muscles may need to be measured. For this example, the pad can be placed in the general region of the desired muscle. As an example, the bicep may be the muscle of interest. To use the pad, the pad is placed in the general area of the bicep and connectors are attached to each of the connection couplers on the pad. The leads attached to the connectors are then coupled to suitable bioelectric measuring equipment. Since the signals are electric potentials, each sensor's reading is taken relative to a base and the reading from one of the sensors can be taken as the base or a separate sensor attached elsewhere on the subject's body can be used as the base. Once the leads are connected to the connection couplers, the various signals are detected and the signals of interest can be isolated if desired.

Figure 9:
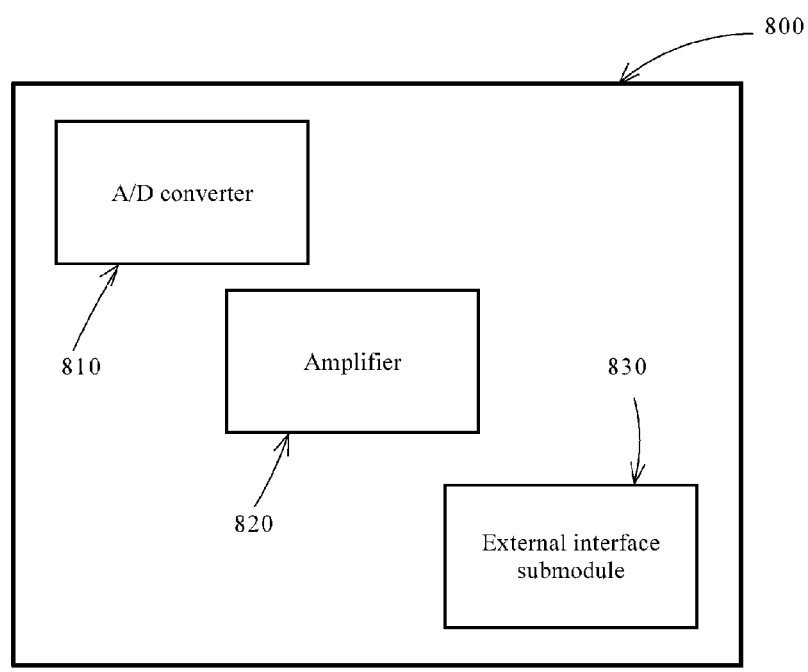
FIG. 9 is a block diagram of a data gathering module which may be used with the pad in FIG. 7.

Since the above example would require multiple leads connected to the pad, potentially leading to a confusion of wires, one alternative is for the provision of a data gathering module. A block diagram of such a data gathering module is illustrated in FIG. 9. The module 800 has a number of components—at least one A/D (analog/digital) converter 810, an amplifier 820, and an external interface submodule 830. The A/D converter 810 converts analog signals to digital signals while the amplifier 820 amplifies weak signals. The data gathering module may be configured to directly couple to each of the connection couplers on the pad. The data gathering module may be equipped with multiple connector couplers, each of which may be usable with the connection couplers on the pad. In one configuration, the data gathering module is equipped with a matrix or array of connection couplers. The array of connection couplers can be configured to directly match and mate with the connector couplers on the pad. Alternatively, the data gathering module may be equipped with a multi-connection connector coupler that mates with or couples with a suitable connector coupler on the pad. For this alternative, instead of single couplers per sensor, a single multi-connection connector coupler can be used on the pad.

Depending on the configuration of the data gathering module, the signal detected by each sensor pad on the pad can be separately amplified and digitally converted by the data gathering module. For such a configuration, multiple instances of the A/D converter and of the amplifier may be present. As an alternative, a single high speed A/D converter and a single amplifier may be used for all the different multiplexed signals from the various sensor pads.

Regarding the external interface submodule, this submodule is used for interfacing with equipment external to the data gathering module. As an example, the data gathering module can provide a bridge between the pad and data processing equipment that can analyze the signals detected and measured by the module. The module couples to all the connection couplers, converts the signals from analog to digital, amplifies these signals, and, using the external interface submodule, passes the converted and amplified signals to the data processing equipment.

It should be noted that the external interface module can use a wired connection between the external equipment and the data gathering module. Alternatively, a wireless connection between the external equipment and the data gathering module can also be used. For this alternative, the submodule may include circuitry for a wireless connection to the external equipment using well-known and widely-accepted communications protocols. As an example, circuitry that allows for a Bluetooth connection between the data gathering module and the external equipment can be included in the submodule.

As yet another alternative, instead of transmitting/transferring the digital data generated by the data gathering module, the digital data can be stored in storage media attached or coupled to the data gathering module. For ease of use, the storage media may be removably coupleable to the data gathering module. A user can thus attach the pad to the subject and then attach the data gathering module to the pad. Once the data gathering module is activated, bioelectric signals are detected by the various sensor pads and these signals are converted and amplified by the A/D converter(s) and the amplifier(s). The data generated can, depending on the configuration, be transmitted to external equipment or be stored in a storage medium attached to the module. The storage medium can then be removed and attached to the external equipment as necessary.

For ease of use, the data gathering module can be configured to communicate with an application running on common smartphones. In one implementation, a data analysis application running on a portable computing device (e.g. a smartphone, tablet computer, laptop computer, etc.) communicates with the data gathering module using a wireless communications link. The data generated is passed to the application and is analyzed, with the results being presented to the user.

Regarding the manufacture of the above devices and systems, it is preferred that the backing on the pad be of a fabric-type backing. It is also preferred that the pad be hypoallergenic and that the backing be free of latex. It is further preferred that the pad as a whole be disposable. The data gathering module may be removably attachable to the pad. Once a pad has been used, the pad can be disposed of and the data gathering module be re-used with another pad. The use of the pad can therefore be hygienic for patient/subjects and convenient for medical personnel.

The pad and the data gathering module can be used in various medical related fields such as Surface electromyography (sEMG), electrocardiography (ECG or EKG), and electroencephalography (EEG).

The method steps of the invention may be embodied in sets of executable machine code stored in a variety of formats such as object code or source code. Such code is described generically herein as programming code, or a computer program for simplification. Clearly, the executable machine code may be integrated with the code of other programs, implemented as subroutines, by external program calls or by other techniques as known in the art.

The embodiments of the invention may be executed by a computer processor or similar device programmed in the manner of method steps, or may be executed by an electronic system which is provided with means for executing these steps. Similarly, an electronic memory means such computer diskettes, CD-Roms, Random Access Memory (RAM), Read Only Memory (ROM) or similar computer software storage media known in the art, may be programmed to execute such method steps. As well, electronic signals representing these method steps may also be transmitted via a communication network.

Embodiments of the invention may be implemented in any conventional computer programming language For example, preferred embodiments may be implemented in a procedural programming language (e.g. "C") or an object oriented language (e.g. "C++", "java", or "C#"). Alternative embodiments of the invention may be implemented as pre-programmed hardware elements, other related components, or as a combination of hardware and software components.

Embodiments can be implemented as a computer program product for use with a computer system. Such implementations may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or electrical communications lines) or a medium implemented with wireless techniques (e.g., microwave, infrared or other transmission techniques). The series of computer instructions embodies all or part of the functionality previously described herein. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies.

It is expected that such a computer program product may be distributed as a removable medium with accompanying printed or electronic documentation (e.g., shrink wrapped software), preloaded with a computer system (e.g., on system ROM or fixed disk), or distributed from a server over the network (e.g., the Internet or World Wide Web). Of course, some embodiments of the invention may be implemented as a combination of both software (e.g., a computer program product) and hardware. Still other embodiments of the invention may be implemented as entirely hardware, or entirely software (e.g., a computer program product).

A person understanding this invention may now conceive of alternative structures and embodiments or variations of the above all of which are intended to fall within the scope of the invention as defined in the claims that follow.

We claim:

1. A circuit comprising:
   at least two inductors, at least one of said inductors being for generating a magnetic field;
   an energy source for providing power to said at least two inductors;
   a plurality of semiconductor switching subsystems for directing power from said energy source to said at least two inductors to generate said magnetic field, said plurality of semiconductor switching subsystems directing energy to said at least two inductors when said subsystems are active;
   wherein
   power is routed from said energy source to said at least two inductors only when all of said subsystems are active;
   when said subsystems are active, said at least two inductors operate as a single inductance;
   when said subsystems are inactive, each of said at least two inductors dissipates its stored energy as a single inductor;
   at least one of said plurality of semiconductor switching subsystems comprises a power semiconductor switching device;
   said circuit is part of a magnetic stimulation device.

2. A circuit according to claim 1 wherein said power semiconductor switching device is an insulated gate bipolar transistor (IGBT).

3. A circuit according to claim 1 wherein said energy source is an energy storage device for storing energy received from a power source.

4. A circuit according to claim 3 wherein said energy storage device is a capacitor.

5. A circuit according to claim 3 wherein said energy storage device is a capacitor bank.

6. A circuit according to claim 1 wherein said at least two inductors comprises a first inductor having a first inductor inductance and a second inductor having a second inductor inductance and wherein said first inductor inductance is lower than said second inductor inductance.

7. A circuit according to claim 6 wherein said first inductor inductance is at a ratio of 1:10 to said second inductor inductance.

8. A circuit according to claim 6 wherein said first inductor inductance is at a ratio of 1:20 to said second inductor inductance.

9. A magnetic stimulation device comprising:
   a first inductor for use in providing a magnetic field adjacent a patient's skull;
   a second inductor for coupling to said first inductor, said second inductor being remote from said patient's skull;

circuitry for providing electromagnetic pulse excitation to said inductors;

an energy source for providing power to said first and second inductors;

a plurality of semiconductor switching subsystems for directing power from said energy source to said first and second inductors to generate said magnetic field, said plurality of semiconductor switching subsystems directing energy to said first and second inductors when said subsystems are active;

wherein power is routed from said energy source to said first and second inductors only when all of said subsystems are active;

when said subsystems are active, said at least two inductors operate as a single inductance;

when said subsystems are inactive, each of said at least two inductors dissipates its stored energy as a single inductor said magnetic field is produced when said first inductor is dissipating its stored energy.

10. A device according to claim 9 wherein at least one of said plurality of semiconductor switching subsystems comprises a power semiconductor switching device and said power semiconductor switching device is an insulated gate bipolar transistor (IGBT).

11. A device according to claim 9 wherein said energy source is an energy storage device for storing energy received from a power source.

12. A device according to claim 11 wherein said energy storage device is a capacitor.

13. A device according to claim 11 wherein said energy storage device is a capacitor bank.

14. A device according to claim 9 wherein said first inductor has a first inductor inductance which is lower than a second inductor inductance of said second inductor.

15. A device according to claim 9 wherein a first inductor inductance of said first inductor is lower than a second inductor inductance of said second inductor and said first inductor inductance is at a ratio of 1:10 to said second inductor inductance.

16. A device according to claim 9 wherein a first inductor inductance of said first inductor is lower than a second inductor inductance of said second inductor and said first inductor inductance is at a ratio of 1:20 to said second inductor inductance.

17. A method for providing magnetic stimulation to an area of mammalian tissue, the method comprising:
a) providing a transcranial magnetic stimulation device having a circuit comprising:
at least two inductors, a treatment inductor for generating a magnetic field being one of said at least two inductors;
an energy source for providing power to said at least two inductors;
a plurality of semiconductor switching subsystems for directing power from said energy source to said at least two inductors, said plurality of semiconductor switching subsystems directing energy to said at least two inductors when said subsystems are active;
b) energizing said energy source to provide power to said at least two inductors;

c) activating said plurality of semiconductor switching subsystems to thereby provide at least one energy pulse to said at least two inductors;
d) deactivating said plurality of semiconductor switching subsystems to thereby individually dissipate energy stored in said at least two inductors;

wherein power is routed from said energy source to said at least two inductors only when all of said subsystems are active;

when said subsystems are active, said at least two inductors operate as a single inductance;

when said subsystems are inactive, each of said at least two inductors dissipates its stored energy as a single inductor;

at least one of said plurality of semiconductor switching subsystems comprises a power semiconductor switching device;

a magnetic field is induced in said mammalian tissue when said stored energy in said treatment inductor is being dissipated.

18. A method according to claim 17 wherein said power semiconductor switching device is an insulated gate bipolar transistor (IGBT).

19. A method according to claim 17 wherein said energy source is an energy storage device for storing energy received from a power source.

20. A method according to claim 17 wherein said at least two inductors comprises a first inductor having a first inductor inductance and a second inductor having a second inductor inductance and wherein said first inductor inductance is lower than said second inductor inductance, said first inductor being said treatment inductor.

21. A method according to claim 20 wherein said first inductor inductance is at a ratio of 1:10 to said second inductor inductance.

22. A method according to claim 20 wherein said first inductor inductance is at a ratio of 1:20 to said second inductor inductance.

23. A method for producing a magnetic field in mammalian tissue, the method comprising:
a) providing a magnetic stimulation device having a circuit comprising:
at least two inductors, a treatment inductor for generating a magnetic field being one of said at least two inductors;
a plurality of semiconductor switching subsystems for charging and discharging said at least two inductors;
b) activating said plurality of semiconductor switching subsystems to charge said at least two inductors;
c) deactivating said plurality of semiconductor switching subsystems to individually discharge said at least two inductors;

wherein when said subsystems are active, said at least two inductors operate as a single inductance;

when said subsystems are inactive, each of said at least two inductors dissipates its stored energy as a single inductor;

a magnetic field is induced in said mammalian tissue when said stored energy in said treatment inductor is being dissipated.

* * * * *